United States Patent
Wang et al.

(10) Patent No.: US 7,303,914 B2
(45) Date of Patent: Dec. 4, 2007

(54) MONOCLONAL ANTIBODY AGAINST HUMAN HEPATOMA AND USE THEREOF

(76) Inventors: Hongyang Wang, 225 Changhai Road, Shanghai (CN) 200438; Xiuju Wu, 880 Xiang Yin Road, Shanghai (CN) 200433

( * ) Notice: Subject to any disclaimer, the term of this patent is extended or adjusted under 35 U.S.C. 154(b) by 114 days.

(21) Appl. No.: 10/544,036

(22) PCT Filed: Jan. 30, 2003

(86) PCT No.: PCT/CN03/00114

§ 371 (c)(1),
(2), (4) Date: Jul. 29, 2005

(87) PCT Pub. No.: WO2004/067571

PCT Pub. Date: Aug. 12, 2004

(65) Prior Publication Data
US 2006/0198845 A1   Sep. 7, 2006

(51) Int. Cl.
*C12N 5/06* (2006.01)
(52) U.S. Cl. ............... 435/332; 530/387.1; 530/388.1; 530/391.7; 424/141.1
(58) Field of Classification Search ............. 350/388.1, 350/391.3, 391.7; 424/141.1; 435/326, 435/332; 530/387.1
See application file for complete search history.

(56) References Cited

U.S. PATENT DOCUMENTS

2002/0090627 A1   7/2002   Meyers

2005/0233392 A1 *  10/2005   Filmus et al.

FOREIGN PATENT DOCUMENTS

| WO | WO 91/09045 | 6/1991 |
|----|-------------|--------|
| WO | WO 9937764 A2 * | 7/1999 |
| WO | WO 01/75121 A2 | 10/2001 |

OTHER PUBLICATIONS

Jones (Pharmacogenomics Journal, 1:126-134, 2001).*
Tosatto et al, (Current Pharmaceutical Design, 12:2067-2086, 2006).*
Fundamental Immunology (William E. Paul, M.D. ed., 3d ed; p. 242, 1993).*
Lage et al (Virchows Arch. 438:567-573, 2001).*
Elgert et al. Immunology: Understanding the Immune System, 1996, p. 59.*
Hsu et al (Cancer Research, 57(22):5179-5184, 1997).*

* cited by examiner

*Primary Examiner*—Stephen L. Rawlings
*Assistant Examiner*—Brad Duffy
(74) *Attorney, Agent, or Firm*—Hamre, Schumann, Mueller & Larson, PC (57) ABSTRACT

The present invention provides a monoclonal antibody MF4C4 against human hepatoma marker antigen. This monoclonal antibody is characterized by high specifically binding to the hepatoma antigen. The present invention also provides MF4C4 immunoglobulins, and the fragments and immunological conjugates thereof, and pharmaceutical compositions containing the immunoglobulins, fragments or immunological conjugates. The invention further provides a kit for detecting hepatoma.

9 Claims, 1 Drawing Sheet

WRL68

SEQUENCE LISTING

```
<160> NUMBER OF SEQ ID NOS: 4

<210> SEQ ID NO 1
<211> LENGTH: 1853
<212> TYPE: DNA
<213> ORGANISM: Homo sapiens
<220> FEATURE:
<221> NAME/KEY: CDS
<222> LOCATION: (109)..(1848)
<223> OTHER INFORMATION:

<400> SEQUENCE: 1
cagcacgtct cttgctcctc agggccactg ccaggcttgc cgagtcctgg gactgctctc      60
gctccggctg ccactctccc gcgctctcct agctccctgc gaagcagg atg gcc ggg     117
                                                    Met Ala Gly
                                                      1 acc gtg cgc acc gcg tgc ttg gtg gtg gcg atg ctg ctc agc ttg gac     165
Thr Val Arg Thr Ala Cys Leu Val Val Ala Met Leu Leu Ser Leu Asp
  5                  10                  15 ttc ccg gga cag gcg cag ccc ccg ccg ccg ccg gac gcc acc tgt         213
Phe Pro Gly Gln Ala Gln Pro Pro Pro Pro Pro Asp Ala Thr Cys
 20                  25                  30                  35 cac caa gtc cgc tcc ttc ttc cag aga ctg cag ccc gga ctc aag tgg     261
His Gln Val Arg Ser Phe Phe Gln Arg Leu Gln Pro Gly Leu Lys Trp
                 40                  45                  50 gtg cca gaa act ccc gtg cca gga tca gat ttg caa gta tgt ctc cct     309
Val Pro Glu Thr Pro Val Pro Gly Ser Asp Leu Gln Val Cys Leu Pro
             55                  60                  65 aag ggc cca aca tgc tgc tca aga aag atg gaa gaa aaa tac caa cta     357
Lys Gly Pro Thr Cys Cys Ser Arg Lys Met Glu Glu Lys Tyr Gln Leu
         70                  75                  80 aca gca cga ttg aac atg gaa cag ctg ctt cag tct gca agt atg gag     405
Thr Ala Arg Leu Asn Met Glu Gln Leu Leu Gln Ser Ala Ser Met Glu
     85                  90                  95 ctc aag ttc tta att att cag aat gct gcg gtt ttc caa gag gcc ttt     453
Leu Lys Phe Leu Ile Ile Gln Asn Ala Ala Val Phe Gln Glu Ala Phe
100                 105                 110                 115 gaa att gtt gtt cgc cat gcc aag aac tac acc aat gcc atg ttc aag     501
Glu Ile Val Val Arg His Ala Lys Asn Tyr Thr Asn Ala Met Phe Lys
                120                 125                 130 aac aac tac cca agc ctg act cca caa gct ttt gag ttt gtg ggt gaa     549
Asn Asn Tyr Pro Ser Leu Thr Pro Gln Ala Phe Glu Phe Val Gly Glu
            135                 140                 145 ttt ttc aca gat gtg tct ctc tac atc ttg ggt tct gac atc aat gta     597
Phe Phe Thr Asp Val Ser Leu Tyr Ile Leu Gly Ser Asp Ile Asn Val
        150                 155                 160 gat gac atg gtc aat gaa ttg ttt gac agc ctg ttt cca gtc atc tat     645
Asp Asp Met Val Asn Glu Leu Phe Asp Ser Leu Phe Pro Val Ile Tyr
    165                 170                 175 acc cag cta atg aac cca ggc ctg cct gat tca gcc ttg gac atc aat     693
Thr Gln Leu Met Asn Pro Gly Leu Pro Asp Ser Ala Leu Asp Ile Asn
180                 185                 190                 195 gag tgc ctc cga gga gca aga cgt gac ctg aaa gta ttt ggg aat ttc     741
Glu Cys Leu Arg Gly Ala Arg Arg Asp Leu Lys Val Phe Gly Asn Phe
                200                 205                 210 ccc aag ctt att atg acc cag gtt tcc aag tca ctg caa gtc act agg     789
Pro Lys Leu Ile Met Thr Gln Val Ser Lys Ser Leu Gln Val Thr Arg
            215                 220                 225 atc ttc ctt cag gct ctg aat ctt gga att gaa gtg atc aac aca act     837
```

```
                  Ile Phe Leu Gln Ala Leu Asn Leu Gly Ile Glu Val Ile Asn Thr Thr
                              230                 235                 240 gat cac ctg aag ttc agt aag gac tgt ggc cga atg ctc acc aga atg            885
Asp His Leu Lys Phe Ser Lys Asp Cys Gly Arg Met Leu Thr Arg Met
        245                 250                 255 tgg tac tgc tct tac tgc cag gga ctg gtg atg gtt aaa ccc tgt ggc            933
Trp Tyr Cys Ser Tyr Cys Gln Gly Leu Val Met Val Lys Pro Cys Gly
260                 265                 270                 275 ggt tac tgc aat gtg gtc atg caa ggc tgt atg gca ggt gtg gtg gag            981
Gly Tyr Cys Asn Val Val Met Gln Gly Cys Met Ala Gly Val Val Glu
                    280                 285                 290 att gac aag tac tgg aga gaa tac att ctg tcc ctt gaa gaa ctt gtg           1029
Ile Asp Lys Tyr Trp Arg Glu Tyr Ile Leu Ser Leu Glu Glu Leu Val
                295                 300                 305 aat ggc atg tac aga atc tat gac atg gag aac gta ctg ctt ggt ctc           1077
Asn Gly Met Tyr Arg Ile Tyr Asp Met Glu Asn Val Leu Leu Gly Leu
            310                 315                 320 ttt tca aca atc cat gat tct atc cag tat gtc cag aag aat gca gga           1125
Phe Ser Thr Ile His Asp Ser Ile Gln Tyr Val Gln Lys Asn Ala Gly
325                 330                 335 aag ctg acc acc act att ggc aag tta tgt gcc cat tct caa caa cgc           1173
Lys Leu Thr Thr Thr Ile Gly Lys Leu Cys Ala His Ser Gln Gln Arg
340                 345                 350                 355 caa tat aga tct gct tat tat cct gaa gat ctc ttt att gac aag aaa           1221
Gln Tyr Arg Ser Ala Tyr Tyr Pro Glu Asp Leu Phe Ile Asp Lys Lys
                    360                 365                 370 gta tta aaa gtt gct cat gta gaa cat gaa gaa acc tta tcc agc cga           1269
Val Leu Lys Val Ala His Val Glu His Glu Glu Thr Leu Ser Ser Arg
                375                 380                 385 aga agg gaa cta att cag aag ttg aag tct ttc atc agc ttc tat agt           1317
Arg Arg Glu Leu Ile Gln Lys Leu Lys Ser Phe Ile Ser Phe Tyr Ser
            390                 395                 400 gct ttg cct ggc tac atc tgc agc cat agc cct gtg gcg gaa aac gac           1365
Ala Leu Pro Gly Tyr Ile Cys Ser His Ser Pro Val Ala Glu Asn Asp
405                 410                 415 acc ctt tgc tgg aat gga caa gaa ctc gtg gag aga tac agc caa aag           1413
Thr Leu Cys Trp Asn Gly Gln Glu Leu Val Glu Arg Tyr Ser Gln Lys
420                 425                 430                 435 gca gca agg aat gga atg aaa aac cag ttc aat ctc cat gag ctg aaa           1461
Ala Ala Arg Asn Gly Met Lys Asn Gln Phe Asn Leu His Glu Leu Lys
                    440                 445                 450 atg aag ggc cct gag cca gtg gtc agt caa att att gac aaa ctg aag           1509
Met Lys Gly Pro Glu Pro Val Val Ser Gln Ile Ile Asp Lys Leu Lys
                455                 460                 465 cac att aac cag ctc ctg aga acc atg tct atg ccc aaa ggt aga gtt           1557
His Ile Asn Gln Leu Leu Arg Thr Met Ser Met Pro Lys Gly Arg Val
            470                 475                 480 ctg gat aaa aac ctg gat gag gaa ggg ttt gaa agt gga gac tgc ggt           1605
Leu Asp Lys Asn Leu Asp Glu Glu Gly Phe Glu Ser Gly Asp Cys Gly
485                 490                 495 gat gat gaa gat gag tgc att gga ggc tct ggt gat gga atg ata aaa           1653
Asp Asp Glu Asp Glu Cys Ile Gly Gly Ser Gly Asp Gly Met Ile Lys
500                 505                 510                 515 gtg aag aat cag ctc cgc ttc ctt gca gaa ctg gcc tat gat ctg gat           1701
Val Lys Asn Gln Leu Arg Phe Leu Ala Glu Leu Ala Tyr Asp Leu Asp
                    520                 525                 530 gtg gat gat gcg cct gga aac agt cag cag gca act ccg aag gac aac           1749
Val Asp Asp Ala Pro Gly Asn Ser Gln Gln Ala Thr Pro Lys Asp Asn
                535                 540                 545
```

-continued

| | | | | | | | | | | | | | | | | |
|---|---|---|---|---|---|---|---|---|---|---|---|---|---|---|---|---|
| gag | ata | agc | acc | ttt | cac | aac | ctc | ggg | aac | gtt | cat | tcc | ccg | ctg | aag | 1797 |
| Glu | Ile | Ser | Thr | Phe | His | Asn | Leu | Gly | Asn | Val | His | Ser | Pro | Leu | Lys | |
| | | | | 550 | | | | | 555 | | | | | 560 | | |
| ctt | ctc | acc | agc | atg | gcc | atc | tcg | gtg | gtg | tgc | ttc | ttc | ttc | ctg | gtg | 1845 |
| Leu | Leu | Thr | Ser | Met | Ala | Ile | Ser | Val | Val | Cys | Phe | Phe | Phe | Leu | Val | |
| | 565 | | | | | 570 | | | | | 575 | | | | | |
| cac | tgact | | | | | | | | | | | | | | | 1853 |
| His | | | | | | | | | | | | | | | | |
| 580 | | | | | | | | | | | | | | | | |

<210> SEQ ID NO 2
<211> LENGTH: 580
<212> TYPE: PRT
<213> ORGANISM: Homo sapiens

<400> SEQUENCE: 2

Met Ala Gly Thr Val Arg Thr Ala Cys Leu Val Val Ala Met Leu Leu
1               5                   10                  15

Ser Leu Asp Phe Pro Gly Gln Ala Gln Pro Pro Pro Pro Pro Pro Asp
            20                  25                  30

Ala Thr Cys His Gln Val Arg Ser Phe Phe Gln Arg Leu Gln Pro Gly
        35                  40                  45

Leu Lys Trp Val Pro Glu Thr Pro Val Pro Gly Ser Asp Leu Gln Val
    50                  55                  60

Cys Leu Pro Lys Gly Pro Thr Cys Cys Ser Arg Lys Met Glu Glu Lys
65                  70                  75                  80

Tyr Gln Leu Thr Ala Arg Leu Asn Met Glu Gln Leu Leu Gln Ser Ala
                85                  90                  95

Ser Met Glu Leu Lys Phe Leu Ile Ile Gln Asn Ala Ala Val Phe Gln
            100                 105                 110

Glu Ala Phe Glu Ile Val Val Arg His Ala Lys Asn Tyr Thr Asn Ala
        115                 120                 125

Met Phe Lys Asn Asn Tyr Pro Ser Leu Thr Pro Gln Ala Phe Glu Phe
    130                 135                 140

Val Gly Glu Phe Phe Thr Asp Val Ser Leu Tyr Ile Leu Gly Ser Asp
145                 150                 155                 160

Ile Asn Val Asp Asp Met Val Asn Glu Leu Phe Asp Ser Leu Phe Pro
                165                 170                 175

Val Ile Tyr Thr Gln Leu Met Asn Pro Gly Leu Pro Asp Ser Ala Leu
            180                 185                 190

Asp Ile Asn Glu Cys Leu Arg Gly Ala Arg Arg Asp Leu Lys Val Phe
        195                 200                 205

Gly Asn Phe Pro Lys Leu Ile Met Thr Gln Val Ser Lys Ser Leu Gln
    210                 215                 220

Val Thr Arg Ile Phe Leu Gln Ala Leu Asn Leu Gly Ile Glu Val Ile
225                 230                 235                 240

Asn Thr Thr Asp His Leu Lys Phe Ser Lys Asp Cys Gly Arg Met Leu
                245                 250                 255

Thr Arg Met Trp Tyr Cys Ser Tyr Cys Gln Gly Leu Val Met Val Lys
            260                 265                 270

Pro Cys Gly Gly Tyr Cys Asn Val Val Met Gln Gly Cys Met Ala Gly
        275                 280                 285

Val Val Glu Ile Asp Lys Tyr Trp Arg Glu Tyr Ile Leu Ser Leu Glu
    290                 295                 300

Glu Leu Val Asn Gly Met Tyr Arg Ile Tyr Asp Met Glu Asn Val Leu
305                 310                 315                 320

```
Leu Gly Leu Phe Ser Thr Ile His Asp Ser Ile Gln Tyr Val Gln Lys
                325                 330                 335

Asn Ala Gly Lys Leu Thr Thr Thr Ile Gly Lys Leu Cys Ala His Ser
            340                 345                 350

Gln Gln Arg Gln Tyr Arg Ser Ala Tyr Tyr Pro Glu Asp Leu Phe Ile
            355                 360                 365

Asp Lys Lys Val Leu Lys Val Ala His Val Glu His Glu Glu Thr Leu
            370                 375                 380

Ser Ser Arg Arg Arg Glu Leu Ile Gln Lys Leu Lys Ser Phe Ile Ser
385                 390                 395                 400

Phe Tyr Ser Ala Leu Pro Gly Tyr Ile Cys Ser His Ser Pro Val Ala
                405                 410                 415

Glu Asn Asp Thr Leu Cys Trp Asn Gly Gln Glu Leu Val Glu Arg Tyr
                420                 425                 430

Ser Gln Lys Ala Ala Arg Asn Gly Met Lys Asn Gln Phe Asn Leu His
                435                 440                 445

Glu Leu Lys Met Lys Gly Pro Glu Pro Val Val Ser Gln Ile Ile Asp
450                 455                 460

Lys Leu Lys His Ile Asn Gln Leu Leu Arg Thr Met Ser Met Pro Lys
465                 470                 475                 480

Gly Arg Val Leu Asp Lys Asn Leu Asp Glu Glu Gly Phe Glu Ser Gly
                485                 490                 495

Asp Cys Gly Asp Asp Glu Asp Glu Cys Ile Gly Gly Ser Gly Asp Gly
                500                 505                 510

Met Ile Lys Val Lys Asn Gln Leu Arg Phe Leu Ala Glu Leu Ala Tyr
                515                 520                 525

Asp Leu Asp Val Asp Asp Ala Pro Gly Asn Ser Gln Gln Ala Thr Pro
                530                 535                 540

Lys Asp Asn Glu Ile Ser Thr Phe His Asn Leu Gly Asn Val His Ser
545                 550                 555                 560

Pro Leu Lys Leu Leu Thr Ser Met Ala Ile Ser Val Val Cys Phe Phe
                565                 570                 575

Phe Leu Val His
            580
```

<210> SEQ ID NO 3
<211> LENGTH: 22
<212> TYPE: DNA
<213> ORGANISM: Artificial Sequence
<220> FEATURE:
<221> NAME/KEY: misc_feature
<222> LOCATION: (1)..(22)
<223> OTHER INFORMATION: primer

<400> SEQUENCE: 3
cggaattctg ccaggatcag at                                              22

<210> SEQ ID NO 4
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: primer

```
<400> SEQUENCE: 4
cgctcgagtc agtgcaccag                                                    20
```

MONOCLONAL ANTIBODY AGAINST HUMAN HEPATOMA AND USE THEREOF

CROSS-REFERENCE TO RELATED APPLICATION

This Application is a Section 371 National Stage Application of International Application No. PCT/CN2003/000114, filed 30 Jan. 2003 and published as WO 2004/067571 A1 on 12 Aug. 2004, the subject matter of which is hereby incorporated by reference in its entirety.

FIELD OF INVENTION

This invention relates to oncology and medical field. In particular, it relates to a monoclonal antibody specifically against human hepatoma and uses thereof.

TECHNICAL BACKGROUND

Hepatocellular carcinoma (HCC) is one of the most common malignancy tumors in human and its incidence is still increasing. This malignancy continues to be a significant cause of cancer morbidity and mortality worldwide. The cause, development, evolution, diagnosis and treatment of hepatoma are of great interest. The early detection of HCC is critical for successful treatment and prognosis.

Currently, AFP is the principal marker for Hepatocellular carcinoma (HCC), which has been used as a serum marker of HCC for many years, and it has been recently used in the genetic diagnosis for HCC hematogenous spreading metastasis. However, said method still has problems in its specificity and its sensitivity. For specificity, the interfering factor for the accuracy of the diagnosis is mainly caused by AFP proteins and the mRNA thereof detected in some patients with cirrhosis or chronic hepatitis. Authoritative statistic suggests that positive rates of serum AFP are 19.8% in patients with acute bilious hepatitis, 19.9% in patients with chronic migratory hepatitis, and 34.4% in chronic active hepatitis, respectively, and up to 44.6% in patients with cirrhosis after hepatitis. The serum AFP concentration of the above non-HCC liver diseases usually is 25-200 ng/ml. Comparing the results of Northern hybridization and immunohistochemical detection of the HCC and noncancerous liver tissue, weak positive AFP expression is usually found in noncancerous liver tissue. Therefore, false positive result of serum AFP protein usually incurs. When part of the liver cells detach into blood because of inflammatory or necrosis, AFP mRNA false positive result will appear in the blood. The research work done by one group of Matsmnura et al. shows that AFP mRNA positive is detected in 15% cirrhosis and 12% chronic hepatitis patients. In other group, Jiang et al. identified 6 AFP mRNA positive out of 11 patients, 1 AFP mRNA positive out of 2 acute hepatitis patients. For sensitivity, the serum AFP is negative in about ⅓ HCC patients (<20 ng/ml). The frequency of positive serum AFP in HCC of well differentiation (I level) and very bad differentiation (IV level) is also quite low, making the detection less efficient for these patients. This indicates the significant rate of missed diagnosis and erroneous diagnosis. Therefore, new markers with higher sensitivity and specificity are needed for improving the early diagnosis of HCC.

Because of the current need of effective method for HCC diagnosis and/or therapy with good specificity, it is urgent to develop specific mAb for HCC, as well as efficient methods for HCC diagnosis and therapy.

SUMMARY OF INVENTION

One purpose of the invention is to provide a monoclonal antibody (mAb) specifically against human hepatoma marker antigen.

Another purpose of the invention is to provide a kit for specifically detecting human hepatoma.

Still another purpose of the invention is to provide an agent for specifically treating human hepatoma.

In the first aspect, the invention provides an immunoglobulin, wherein said immunoglobulin specifically binds to MXR7 protein. Preferably, the immunoglobulin specifically binds to a MXR7 protein with N-terminal deletion, e.g., a MXR7 protein in which the N terminal 50-100 amino acids and preferably 50-80 amino acids are deleted.

More preferably, the immunoglobulin binds to MXR7 protein having the amino acid sequence of SEQ ID NO:2, or a MXR7 protein in which the N terminal 55 amino acids are deleted.

In an embodiment of the invention, the immunoglobulin is monoclonal antibody.

In another embodiment of the invention, the immunoglobulin is produced by mouse hybridoma cell line MF4C4, CCTCC No.C200111.

In the second aspect, the invention provides an immunological conjugate, which comprises an immunoglobulin, specifically binding to MXR7 protein and a conjugating moiety selected from the group consisting of drug, toxin, cytokine, radionuclide, and enzyme.

In the third aspect, the invention provides a hybrid cell for producing monoclonal antibody which is mouse hybridoma cell line MF4C4, CCTCC No.: C200111.

In the fourth aspect, the invention provides a kit for detecting hepatoma, which comprises the above immunoglobulin or immunological conjugate, or the active fragment thereof.

In the fifth aspect, the invention provides a pharmaceutical composition, which comprises the above immunoglobulin or immunological conjugate, and a pharmaceutically acceptable carrier.

DETAILED DESCRIPTION OF INVENTION

After comprehensive and extensive study, the inventors have found that MXR7 gene is closely correlated with HCC and may serve as a sensitive and specific marker for HCC. Based on said discovery, MXR7 gene was isolated from human placenta cDNA library and expressed, and a hybridoma cell line monoclonal antibody (mAb), anti-human HCC monoclonal antibody MF4C4 was developed. The mAb was proved stable and bound to HCC antigen with high specificity.

MXR7 was cloned by the differential display method (Lage, 1996). At same time, we cloned MXR7 gene from HCC cDNA library while we were studying HCC specific sensitive marker gene. The full-length cDNA sequence of MXR7 gene is 2263 bp, located at Xq26, consists of 8 exons, and encodes 580 aa heparin sulfate proteoglycan. Said marker gene has a molecular weight of 66 kDa. It is bound to the cell surface through a glycosylphosphati-dylinositol (GPI) anchor. MXR7 gene belongs to proteoglycan family. It is highly expressed in mesoblast, synthesized in lung, liver, and kidney of embryo, and also is expressed in placenta tissue at low level. There are no expressions in other tissues of embryo. MXR7 is deemed to regulate developmental morphogenesis and growth. Once finishing morphogenesis, the expression is negatively regulated and cannot be detected after ablactation.

The study reported that MXR7 correlated closely with oncogenesis and progression of HCC. Not only it is highly detected in the early period of HCC, but also the detectable rate increases with the progression of HCC. The inventor detected that the frequency of MXR7 mRNA expression was 76.7% (23/30) in HCC tissues, in which 13.3% (4/30) noncancerous liver tissue had weak positive expression of MXR7, other 7 HCC tissues were MXR7 expression negative, whose MXR7 expression in noncancerous liver tissue was negative. It is important that the frequency of MXR7 mRNA expression in serum AFP positive patients of HCC was 88%, but still there were 73% MXR7 mRNA expression positive HCC patients whose sera were AFP negative. In small HCC (<3 cm) HCC, the frequency of MXR7 mRNA expression was 77%, significantly higher than that with elevated serum AFP (43%) and AFP mRNA expression in HCC (41%). MXR7 expression was not detected in hepatocellular adenoma, cholangiocarcinoma, liver metastatic carcinomas, 12 common non-HCC solid carcinomas and 21 non-HCC cell lines. These findings indicate that MXR7 specifically expressed in HCC, whose specificity is significantly higher than presently used HCC marker AFP. MXR7 is more sensitive and has higher detection rate than AFP, especially in AFP-negative HCC patient. Therefore, MXR7 is a new HCC marker which can be used with AFP additionally and together in early diagnosis of HCC.

On the other hand, as the expression of MXR7 is gradually increased followed HCC progression, it will be an important target gene to predict prognosis of HCC and to resist metastasis or recrudescent of HCC.

MXR7 is one of the two X chromosome related gene in HCC. The familial aggregation and the heredity of susceptibility of the patients with HCC are well documented and the frequency of HCC among males is about 10 folds of females. The epidemiology study shows that the effect of heredity on maternal side is much greater than that of paternal one. Whether MXR7 gene is the main gene of the heredity of HCC susceptibility or not is still in research.

MXR7 correlated closely with HCC, but its molecular mechanism is not clear, which needs further research. MXR7 gene is highly expressed in embryonic liver and is silent in adult liver, but restored in HCC, whose space and time profile is similar to the expression of AFP gene. However, MXR7 mRNA expression is more sensitive than AFP and the positive rate is higher. Said gene binds to the cell surface by GPI anchoring protein, and is co-receptor of IGF-2. Therefore, it can be released into blood like the other members of this family and be detected in blood of HCC patients. Therefore, it can be used as specific marker for early serum diagnosis of HCC.

Based on the above research, the inventors have prepared anti-human MXR7 mAb MF4C4 by hybridoma technology.

MF4C4 mAb or its fragments of the present invention may be used in diagnostic imaging of radiological location of HCC and in immunotherapy. For example, the MF4C4 mAb or the fragments thereof can be directly or indirectly linked with chemotherapeutic agents or radiotherapeutic agents, thus directly targeting to cancer cells.

The present invention includes: mAb comprising the corresponding amino acid sequence of MF4C4 mAb, mAb with MF4C4 mAb variable domain chains, and other protein comprising these chains, or protein conjugates, and fusion expression product. Particularly, the present invention comprises any protein, protein conjugates, and fusion expression product comprising light and heavy chain with hypervariable domains (complementary decision region, CDR) (immune-linked and fusion expression products), as long as said CDR is identical or at least 90% homogenous to the CDR of the light and heavy chain of the present invention.

As known by the skilled in the art, those immune-linked or fusion expression products include drugs, toxins, cytokines, isotopes, enzymes and other conjugates formed by linking the diagnosis or therapeutical moieties with MF4C4 mAb or the fragments thereof. The present invention also includes antigens and cell surface marker binding to MF4C4 mAb or the fragments thereof.

The term "Immune toxins" used herein refers to molecules specially binding with and killing the target cells. For example, those immune-linked or fusion expression products are selected from drugs, toxins, cytokines, isotopes or other conjugates formed by linking the therapeutically moieties with MF4C4 mAb or the fragments thereof, such as $^{131}$I-MF4C4, MTX-MF4C4.

The sequences of heavy chains and light chains of MF4C4 mAb can be analyzed by routine methods. The hypervariable region and complementarity determining region (CDR) of MF4C4 mAb V chain of particular interest, because they are related partially to the binding of antigens. Therefore, the present invention includes those molecules of heavy or light chains with CDR domains, as long as said CDR is at least 90% (preferably at least 95%) homologous with MF4C4 mAb.

The present invention includes not only intact monoclonal, but also immunologically-active antibody fragments, e.g., a Fab' or (Fab)$_2$ fragment, an antibody heavy chain, an antibody light chain, a genetically engineered single chain Fv molecule, or a chimerical antibody, e.g., an antibody which contains the binding specificity of a murine antibody, but the remaining portion of which is of human origin.

The present invention also provides a cDNA encoding the hepatoma marker antigen. The full-length antigen nucleotide sequence or its fragment can be prepared by PCR amplification, recombinant method and synthetic method. For PCR amplification, one can obtain said sequences by designing primers based on the hepatoma marker antigen nucleotide sequence disclosed herein, especially the ORF, and using DNA prepared by routine techniques in the art as a template. When the sequence is long, it is usually necessary to perform two or more PCR amplifications and link the amplified fragments together correctly.

The present invention also provides the molecules for encoding the immunoglobulin or its fragments. The sequences of these molecules can be obtained by the conventional techniques and using mouse hybridoma cell line MF4C4 (CCTCC No.: C200111). Moreover, the encoding sequences of light chain and heavy chain may be fused together to form a single chain antibody.

Once the sequence is obtained, one can produce lots of the sequences by recombinant methods. Usually, said sequence is cloned into a vector, which is then transformed into a host cell. The sequence is isolated from the amplified host cells using conventional techniques.

Further, the sequence can be synthesized, especially when the fragment is short. Typically, several small fragments are synthesized and linked together to obtain a long sequence.

It is completely feasible to chemically synthesize the DNA sequence encoding the protein of invention, or the fragments or derivatives thereof. Then, these DNA can be introduced into various DNA molecules (e.g., vector) and cells known in the art. In addition, the mutation can be introduced into the protein sequence by chemical synthesis.

The invention further relates to a vector comprising the above DNA sequence and suitable promoter or regulatory sequence, which can be used to transform suitable host cell to make it express protein.

The host cell includes prokaryote, e.g., bacteria; primary eukaryote, e.g., yeast; advanced eukaryotic, e.g., mammalian cells. The representative examples are bacterial cells, e.g., E. coli, Streptomyces, Salmonella typhimurium; fungal cells, e.g., yeast; plant cells; insect cells e.g., Drosophila S2 or Sf9; animal cells e.g., CHO, COS7, 293 cell or Bowes melanoma, etc.

Recombinant transformation of host cell with the DNA might be carried out by conventional techniques known to the artisans. Where the host is prokaryotic, e.g., E. coli, the competent cells capable of DNA uptake, can be prepared from cells harvested after exponential growth phase and subsequently treated by the $CaCl_2$ method using known procedures. Alternatively, $MgCl_2$ can be used. The transformation can also be carried out by electroporation. When the host is an eukaryote, transfection of DNA such as calcium phosphate co-precipitates, conventional mechanical procedures e.g., micro-injection, electroporation, or liposome-mediated transfection may be used.

The transformants are cultured conventionally to express the polypeptide encoded by the gene of the invention. According to the used host cells, the medium for cultivation can be selected from various conventional mediums. The host cells are cultured under a condition suitable for its growth until the host cells grow to an appropriate cell density. Then, the selected promoter is induced by appropriate means (e.g., temperature shift or chemical induction) and cells are cultured for an additional period.

In the above methods, the recombinant polypeptide may be included in the cells, or expressed on the cell membrane, or secreted out. If desired, the physical, chemical and other properties can be utilized in various isolation methods to isolate and purify the recombinant protein. These methods are well-known to the artisans and include, but are not limited to conventional renaturation treatment, treatment by protein precipitant (e.g., salt precipitation), centrifugation, cell lysis by osmosis, sonication, supercentrifugation, molecular sieve chromatography or gel chromatography, adsorption chromatography, ion exchange chromatagraphy, HPLC, and any other liquid chromatagraphy, and the combination thereof.

Further, the present invention provides a kit for detecting hepatoma, which comprises the above immunoglobulin or immunological conjugate, or the active fragments thereof. In an embodiment, the clinical test on human hepatoma diagnosis kit was carried out on 193 cases and the positive rate in detection was 74%.

The present invention also provides a pharmaceutical composition, which comprises the above immunoglobulin or immunological conjugate in combination with a pharmaceutically acceptable carrier. Usually, these substances are formulated with a non-toxic, inert and pharmaceutically acceptable aqueous carrier. The pH typically is about 5-8, preferably 6-8, although pH may alter according to the property of the formulated substances and the diseases to be treated. The formulated pharmaceutical composition is administrated in conventional routes including, but not limited to, intraperitoneal, intravenous, or topical administration.

The pharmaceutical composition of the invention can be directly used for curing hepatoma. Moreover, it can be administrated in combination with other medicaments, e.g, IFN-α, IFN-β, TNF-α etc.

The invention also provides a pharmaceutical composition comprising safe and effective amount of the above immunoglobulin or immunological conjugate in combination with a pharmaceutically acceptable carrier or excipient. Such a carrier includes but is not limited to saline, buffer solution, glucose, water, glycerin, ethanol, or the combination thereof. The pharmaceutical formulation should be suitable for delivery method. The pharmaceutical composition may be in the form of injections which are made by conventional methods, using physiological saline or other aqueous solution containing glucose or auxiliary substances. The pharmaceutical compositions in the form of tablet or capsule may be prepared by routine methods. The pharmaceutical compositions, e.g., injections and solutions, should be manufactured under sterile conditions. The active ingredient is administrated in therapeutically effective amount, e.g., about 1 ug-5 mg/kg body weight per day. Moreover, the polypeptide of invention can be administrated together with other therapeutic agents.

When using pharmaceutical composition, the safe and effective amount of the MF4C4 conjugate is administrated to mammals. Typically, the safe and effective amount is at least about 10 ug/kg body weight and less than about 8 mg/kg body weight in most cases, and preferably about 10 ug-1 mg/kg body weight. Certainly, the precise amount depends upon various factors, such as delivery methods, the subject health, etc., and is within the judgment of the skilled clinician.

The invention provides not only hybridoma cell lines which produce high titers of anti-human MXR7 mAb, but also the mAb itself for detecting the amount of MXR7 proteins in the serum of clinic HCC patients. According to the search of references, up to date no similar studies were reported worldwide for the same work. The present mAb can successfully serve in serum diagnosis (suitable for clinic use) for primary HCC, particular for the identification of α-FP negative liver cancer and the prediction of the prognosis of HCC patients. Furthermore, the present mAb can be used in immunotherapy of HCC, to improve the general therapeutic effect of liver cancer.

The invention is further illustrated by the following examples. These examples are only intended to illustrate the invention, but not to limit the scope of the invention. For the experimental methods in the following examples, they are performed under routine conditions, e.g., those described by Sambrook. et al., in Molecule Clone: A Laboratory Manual, New York: Cold Spring Harbor Laboratory Press, 1989, or as instructed by the manufacturers, unless otherwise specified.

EXAMPLE 1

Obtaining cDNA Sequences Encoding Human MXR7

The DNA primers of upstream and downstream the open reading frame (ORF) were designed and synthesized according to the MXR7 gene sequence. The following MXR7 gene encoding sequence (SEQ ID NO: 1) was isolated by amplifying human placenta cDNA library.

```
                                                                  (SEQ ID NO: 1)
   1 cagcacgtct cttgctcctc agggccactg ccaggcttgc cgagtcctgg gactgctctc 61 gctccggctg ccactctccc gcgctctcct agctccctgc gaagcaggat ggccgggacc 121 gtgcgcaccg cgtgcttggt ggtggcgatg ctgctcagct tggacttccc gggacaggcg 181 cagccccgc cgccgccgcc ggacgccacc tgtcaccaag tccgctcctt cttccagaga 241 ctgcagcccg gactcaagtg ggtgccagaa actcccgtgc caggatcaga tttgcaagta 301 tgtctcccta agggcccaac atgctgctca agaaagatgg aagaaaaata ccaactaaca 361 gcacgattga acatggaaca gctgcttcag tctgcaagta tggagctcaa gttcttaatt 421 attcagaatg ctgcggtttt ccaagaggcc tttgaaattg ttgttcgcca tgccaagaac 481 tacaccaatg ccatgttcaa gaacaactac ccaagcctga ctccacaagc ttttgagttt 541 gtgggtgaat ttttcacaga tgtgtctctc tacatcttgg gttctgacat caatgtagat 601 gacatggtca atgaattgtt tgacagcctg tttccagtca tctataccca gctaatgaac 661 ccaggcctgc ctgattcagc cttggacatc aatgagtgcc tccgaggagc aagacgtgac 721 ctgaaagtat ttgggaattt ccccaagctt attatgaccc aggtttccaa gtcactgcaa 781 gtcactagga tcttccttca ggctctgaat cttggaattg aagtgatcaa cacaactgat 841 cacctgaagt tcagtaagga ctgtggccga atgctcacca gaatgtggta ctgctcttac 901 tgccagggac tggtgatggt taaaccctgt ggcggttact gcaatgtggt catgcaaggc 961 tgtatggcag gtgtggtgga gattgacaag tactggagag aatacattct gtcccttgaa 1021 gaacttgtga atggcatgta cagaatctat gacatggaga acgtactgct tggtctcttt 1081 tcaacaatcc atgattctat ccagtatgtc cagaagaatg caggaaagct gaccaccact 1141 attggcaagt tatgtgccca ttctcaacaa cgccaatata gatctgctta ttatcctgaa 1201 gatctcttta ttgacaagaa agtattaaaa gttgctcatg tagaacatga agaaacctta 1261 tccagccgaa gaagggaact aattcagaag ttgaagtctt tcatcagctt ctatagtgct 1321 ttgcctggct acatctgcag ccatagccct gtggcggaaa acgacaccct tgctggaat 1381 ggacaagaac tcgtggagag atacagccaa aaggcagcaa ggaatggaat gaaaaaccag 1441 ttcaatctcc atgagctgaa aatgaagggc cctgagccag tggtcagtca aattattgac 1501 aaactgaagc acattaacca gctcctgaga accatgtcta tgcccaaagg tagagttctg 1561 gataaaaacc tggatgagga agggtttgaa agtggagact gcggtgatga tgaagatgag 1621 tgcattggag gctctggtga tggaatgata aagtgaaga atcagctccg cttccttgca 1681 gaactggcct atgatctgga tgtggatgat gcgcctggaa acagtcagca ggcaactccg 1741 aaggacaacg agataagcac ctttcacaac ctcgggaacg ttcattcccc gctgaagctt 1801 ctcaccagca tggccatctc ggtggtgtgc ttcttcttcc tggtgcactg act
```

The full-length of MXR7 was 1853 bp, wherein the ORF was located in 109-1848 nt, encoding heparin sulfate proteoglycan of 580 amino acids having the amino acid sequence of SEQ ID NO: 2. The molecule weight of said protein was 66 kDa. Said protein bound to the cell membrane through a glycosylphosphati-dylinositol (GPI) anchor, belonging to proteoglycan family.

```
                                                          (SEQ ID NO: 2)
MAGTVRTACL VVAMLLSLDF PGQAQPPPPP PDATCHQVRS FFQRLQPGLK  50

WVPETPVPGS DLQVCLPKGP TCCSRKMEEK YQLTARLNME QLLQSASMEL 100

KFLIIQNAAV FQEAFEIVVR HAKNYTNAMF KNNYPSLTPQ AFEFVGEFFT 150

DVSLYILGSD INVDDMVNEL FDSLFPVIYT QLMNPGLPDS ALDINECLRG 200

ARRDLKVFGN FPKLIMTQVS KSLQVTRIFL QALNLGIEVI NTTDHLKFSK 250

DCGRMLTRMW YCSYCQGLVM VKPCGGYCNV VMQGCMAGVV EIDKYWREYI 300

LSLEELVNGM YRIYDMENVL LGLFSTIHDS IQYVQKNAGK LTTTIGKLCA 350

HSQQRQYRSA YYPEDLFIDK KVLKVAHVEH EETLSSRRRE LIQKLKSFIS 400

FYSALPGYIC SHSPVAENDT LCWNGQELVE RYSQKAARNG MKNQFNLHEL 450

KMKGPEPVVS QIIDKLKHIN QLLRTMSMPK GRVLDKNLDE EGFESGDCGD 500

DEDECIGGSG DGMIKVKNQL RFLAELAYDL DVDDAPGNSQ QATPKDNEIS 550

TFHNLGNVHS PLKLLTSMAI SVVCFFFLVH                       580
```

Compared with published MXR7 gene, there was a mutation of A to G (amino acid M to V) in position 913.

EXAMPLE 2

The Expression of Human MXR7 Protein Fragment

The inventors carried out many times of trials for the expression of MXR7, and found that depletion of $NH_2$-terminal portion of MXR7 protein could make expression effective and purified the MXR7 protein.

The following PCT primers were used in this example:
Primer 1: 5'-cggaattctgccaggatcagat-3'(SEQ ID NO: 3)
Primer 2: 5'-cgctcgagtcagtgcaccag-3'(SEQ ID NO: 4)
By PCR, human MXR7 cDNA (523aa, N-terminal 57 aa deleted) was cloned from human placenta cDNA library (CLONTECH, Human Placenta cDNA), linked to 6×His fusion expression vector pPROEX HT(GIBCO BRL, 10711-018). After induced by IPTG, the protein was purified by Ni-NTA Sepharose® affinity chromatography.

EXAMPLE 3

The Preparation and Purification of MF4C4 mAb (1) The Preparation of Hybridoma
Balb/c mice were immunized with purified MXR7 protein obtained in Example 2. At the first immunization, same volume of Freund's complete adjuvant and antigen (100 μl, 50-100 ug) were mixed, emulsified completely and i.p. injected. 3 weeks later, the mice were booster immunized by half amount of antigen with Freund's incomplete adjuvant. The injection volume and method were the same above. After the serum potency of the mice reaches the requirement, cell fusion was prepared. 3 days before the fusion, the mouse was administered with impact immunization (50 ug antigen).

While immunizing the mice, mice hybridoma cells P3X63Ag8.653 (ATCC CRL-1580) was prepared.
Sensitized B lymphocyte were fused with hybridoma cells, and selectively cultured by HAT medium (mice celiac macrophage was used as feeder cell).
Then, the supernatant of the culture medium of hybridoma cells was assayed by ELISA: ELISA plates were coated with 100 μl/well purified MXR7 protein (2 μg/ml) and incubated overnight at 4° C. After blocking at room temperature, 100 μl of the supernatant to be analyzed was added and incubated for 1 h at 37° C., and washed for 3 times. Anti-mice IgG-HRP was added as the second antibody, incubated for 45 min at 37° C. The second antibody was discarded and the assay mixture was washed for 3 times. 50 μl substrate developer was added, standing 5 minutes at room temperature, and 50 μl of termination solution was added. Results were read at 450 nm wavelength by ELISA detector. Positive was identified for those with OD value 2 times higher than negative controls.

Then, positive hybridoma cells were cloned (limited dilution, using mice celiac macrophage as feeder cells). After 2-3 times of clonal culture, hybridoma cell clones producing high potency mAbs was obtained. The hybridoma cell lines were proliferated, frozen and deposited.

A positive hybridoma, human hepatocellular carcinoma MF4C4, was deposited in Typical Culture Collection of China (CCTCC, address: Wuhan University, Wuhan 430072, China) on Sep. 5, 2001 with an Accession Number of No. C200111.

(2) Preparation and Purification of MF4C4 mAb
Ascites was collected after intraperitoneal injection with the above hybridoma cell line MF4C4 to mice, and mAb was extracted from the ascites.

Purification of mAb MF4C4:
Protein A affinity chromatography was used. Protein A affinity chromatography column was prepared and equilibrated with PBS. Ascites or hybridoma cell culture supernatant with anti-MXR7 mAb were loaded, washed with PBS until OD close to zero. The mAb was eluted with 50 mmol/L glycine-HCl (pH2.3) buffer, and the eluent was collected. The OD value of each fraction was read. The eluted products at peek value were collected, dialyzed and concentrated for preparing enzyme-linked antibody.

EXAMPLE 4

Identification of MF4C4 Monoclonal Antibody

Figure 1:
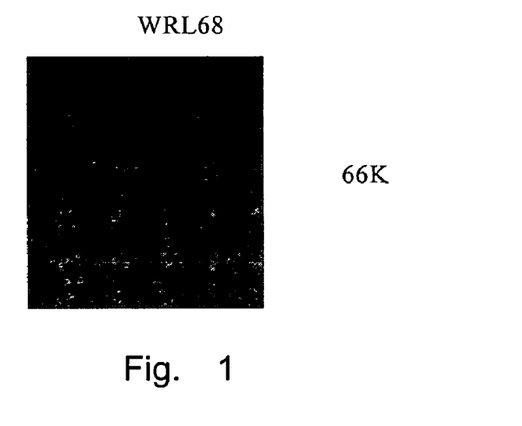
FIG. 1 shows the MXR7 protein expression in embryo liver cells by using monoclonal antibody MF4C4 in Western blotting.
Figure 2:
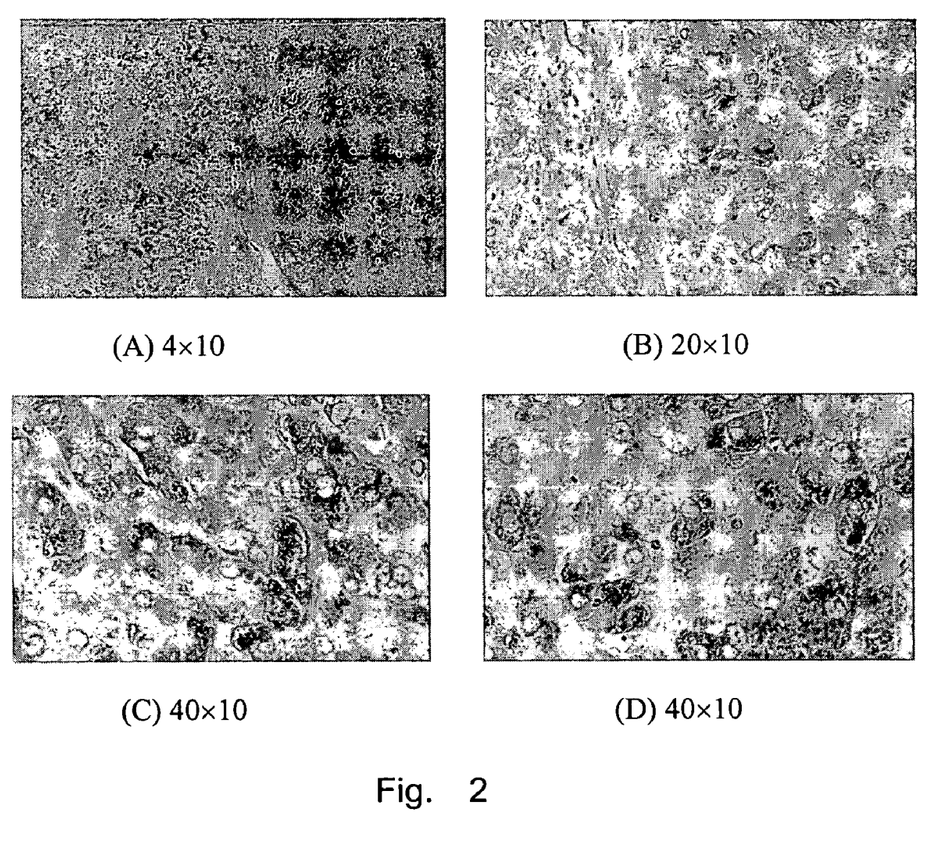
FIG. 2A, 2B, 2C and 2D shows the MXR7 protein expression in HCC tissue by using monoclonal antibody MF4C4 in immunohistochemical detection.

The expression of MXR7 protein in human embryo liver cells was detected by Western blotting experiment with the MF4C4 mAb prepared in Example 3. Results showed that the mAb specifically bound to a band located at 66KD (FIG. 1).

Immunohistochemical blotting of HCC tissue section was undertaken by common method using MF4C4 mAb. The results in FIG. 2 (A-D different magnification scales) show clear color in cytoplasm area of progressive cancer nests of the envelope region of tumor, suggesting the better specificity and sensitivity of anti-MXR7 mAb.

EXAMPLE 5

Using indirect competitive ELISA, the amount of MXR7 protein in the serums of HCC patients (100 cases), patients with non-HCC hepatobiliary disorders (43 cases), and normal people (50 cases) were tested using M4F4 mAb prepared in Example 3.

The results indicated that MXR7 protein was highly expressed in 74% of the serum of HCC patients. However, the positive rate of MXR7 protein in patients with non-HCC hepatobiliary disorders was only 18.60%, and the protein expression level was low than HCC patients. In the serum of normal people, the amount of MXR7 protein was very low. This indicated that anti-MXR7 mAb has high sensitivity and specificity.

All the documents cited herein are incorporated into the invention as reference, as if each of them is individually incorporated. Further, it is appreciated that, in the above teaching of the invention, the skilled in the art can make certain changes or modifications to the invention, and these equivalents are still within the scope of the invention defined by the appended claims of the present application.

INDICATIONS RELATING TO A DEPOSITED MICROORGANISM (PCT Rule 13bis)

A. The indications made below relate to the microorganism referred to in the description on page ___9___, line ___28-30___.

B. IDENTIFICATION OF DEPOSIT  Further deposits are identified on an additional sheet ☐

Name of depositary institution

China Center for Type Culture Collection (CCTCC)

Address of depositary institution (including postal code and country)

Wuhan 430072, China

| Date of deposit 05 September 2001 | Accession Number CCTCC 200111 |

C. ADDITIONAL INDICATIONS (leave blank if not applicable)  This information is continued on an additional sheet ☐

D. DESIGNATED STATES FOR WHICH INDICATIONS ARE MADE (if the indications are not for all designated States)

E. SEPARATE FURNISHING OF INDICATIONS (leave blank if not applicable)

The indications listed below will be submitted to the International Bureau later (specify the general nature of the indications e.g., "Accession Number of Deposit")

| For receiving Office use only | For International Bureau use only |
|---|---|
| [X] This sheet was received with the international application | [ ] This sheet was received by the International Bureau on: |
| Authorized officer | Authorized officer |

Form PCT/RO/134 (July 1992)

What is claimed is:

1. A monoclonal antibody which specifically binds to MXR7 protein and antigen-binding fragments thereof, wherein the monoclonal antibody is produced by mouse hybridoma cell line MF4C4, CCTCC No. C200111 and wherein the MXR7 protein comprises the amino acid sequence of SEQ ID NO: 2 or the amino acid sequence of residues 58-580 of SEQ ID NO: 2.

2. The monoclonal antibody of claim 1 wherein the MXR7 protein consists of the amino acid sequence of SEQ ID NO: 2.

3. A monoclonal antibody which is produced by mouse hybridoma cell line MF4C4, CCTCC No.C200111.

4. An immunological conjugate which comprises the monoclonal antibody of claim 1 conjugated to a moiety selected from the group consisting of drug, toxin, cytokine, radionuclide, and enzyme.

5. A hybrid cell for producing a monoclonal antibody which is mouse hybridoma cell line MF4C4, CCTCC No.: C200111.

6. A kit for detecting hepatoma which comprises the monoclonal antibody of claim 1.

7. A pharmaceutical composition, which comprises the monoclonal antibody of claim 1, and a pharmaceutically acceptable carrier.

8. A method of detecting and/or quantifying the amount of MXR7 protein comprising the following steps:

contacting the monoclonal antibody of claim 1 or the antigen-binding fragments thereof with a serum sample; and detecting the presence and/or quantifying the amount of MXR7 protein in the serum sample, wherein the MXR7 protein comprises the amino acid sequence of SEQ ID NO: 2.

9. The method of claim 8 wherein the serum sample is from human.

* * * * *